(12) United States Patent
Romet-Lemonne et al.

(10) Patent No.: US 6,258,358 B1
(45) Date of Patent: Jul. 10, 2001

(54) TARGETED IMMUNOSTIMULATION WITH BISPECIFIC REAGENTS

(75) Inventors: Jean Loup Romet-Lemonne, Gif-sur-Yvette (FR); Michael W. Fanger, Lebanon, NH (US); Paul M. Guyre, Hanover, NH (US); Edmund J. Gosselin, North Haverhill, NH (US)

(73) Assignee: Medarex, Inc., Princeton, NJ (US)

( * ) Notice: Subject to any disclaimer, the term of this patent is extended or adjusted under 35 U.S.C. 154(b) by 0 days.

(21) Appl. No.: 08/453,500

(22) Filed: May 30, 1995

Related U.S. Application Data

(62) Division of application No. 08/249,669, filed on May 26, 1994, which is a continuation of application No. 07/874,622, filed on Apr. 27, 1992, now abandoned, which is a continuation-in-part of application No. 07/593,083, filed on Oct. 5, 1990, now abandoned.

(51) Int. Cl.$^7$ .......................... A61K 39/395; A61K 38/00; A61K 39/00; C12P 21/08
(52) U.S. Cl. ..................... 424/136.1; 424/134.1; 424/135.1; 424/178.1; 424/192.1; 424/193.1; 424/277.1; 530/387.1; 530/387.3
(58) Field of Search ............................. 424/136.1, 134.1, 424/135.1, 178.1, 192.1, 193.1, 277.1; 530/387.3, 387.1

(56) References Cited

U.S. PATENT DOCUMENTS

| | | |
|---|---|---|
| 4,474,893 | 10/1984 | Reading ............................. 436/547 |
| 4,676,980 | 6/1987 | Segal et al. ............................ 424/85 |
| 4,950,480 | 8/1990 | Barber et al. ....................... 424/85.8 |
| 4,954,617 | 9/1990 | Fanger et al. ........................ 530/387 |

FOREIGN PATENT DOCUMENTS

| | | |
|---|---|---|
| WO 8800052 | 1/1988 | (WO) . |
| WO 8906544 | 7/1989 | (WO) . |

OTHER PUBLICATIONS

Farci et al Science vol. 258:135–140, 1992.*
Bukh et al Seminars in Liver Disease vol. 15 No. 1 41–63, 1995.*
Fahey et al Clin Exp Immunol vol. 88 1–5, 1992.*
Fox Bio/Technology vol. 12:128, 1994.*
Bangham, A.D., et al., (1995), "Diffusion of Univalent Ions Across the Lamellae of Swollen Phospholipids," *J. Mol. Biol.*, vol. 13, pp. 238–252.
Borrebaeck, C., et al., (1988), "Human Monoclonal Antibodies Produced by Primary in Vitro Immunization of Peripheral Blood Lymphocytes," *PNAS*, vol. 85, pp.3995–3999.
Brennan, M., et al., (1985), "Preparation of Bispecific Antibodies by Chemical Recombination of Monoclonal Immunoglobulin G1 Fragments," *Science*, vol. 229, pp. 81–83.
Celis, E. and Chang, T.W. (1984), "Antibodies to Hepatitis B Surface Antigen Potentiate the Response of Human T Lymphocyte Clones to the Same Antigen," *Science*, vol. 224, pp. 297–299.
Chang, T., (1985), "Regulation of Immune Response by Antibodies: the Importance of Antibody and Monocyte Fc Receptor Interaction in T–cell Activation," *Immunol. Today*, vol. 6, No. 8, pp. 245–259.
Eynon, E., et al., (1992), "Small B Cells as Antigen–presenting Cells in the Induction of Tolerance to Soluble Protein Antigens," *J. Exp. Med.*, vol. 175, p. 131–138.
Germain, R., (1991), "The Second Class Story," *Nature*, vol. 353, pp. 605–607.
Gilliland, L.K., et al., (Oct. 22–25, 1989), "Bispecific Monoclonal Antibodies and Antibody Heteroconjugates for Enhancement of T Cell Activation and for Targeting Effector Activity Against HIV–Infected Cells," *Abstract from meeting in Annapolis*, p. 35.
Gilliland, L.K. et al., (Sep. 25, 1985), "Bispecific Monoclonal Antibodies and Antibody Heteroconjugates for Enhancement of T Cell Activation and for Targeting Effector Activity Against HIV–Infected Cells," *Abstract from Meeting in Annapolis*, p. 35.
Glennie, M., et al., (1987), "Preparation and Performance of Bispecific F (ab'γ)2 Antibody Containing Thioether–Linked Fab'γ Fragments," *J. Immunol.*, vol. 139, pp. 2367–2375.
Gosselin, E., et al., (1990), "The Monoclonal Antibody 41H16 Detects the Leu 4 Responder Form of Human FcγRII[1]," *J. Immunol.*, vol. 144, No. 5, pp. 1817–1822.
Guyre, P.M., et al., (1988), "Glucocorticoid Effects on the Production and Actions of Immune Cytokines," *J. Steroid Biochem.*, vol. 30, No. 1–6 pp. 89–93.
Guyre, P.M., et al., (1989), "Monoclonal Antibodies That Bind to Distinct Epitopes on FcγRI are able to Trigger Receptor Function," *J. Immunol.*, vol. 143, pp. 1650–1655.
Hird, et al., (1990), "The Search for the Predisposing Genes," *Genes and Cancer*, p. 101–104.
Huston, J., et al., (1988), "Protein Engineering of Antibody Binding Sites: Recovery of Specific Activity in an Anti–Digoxin Single– chain Fv Analogue Produced in *Escherichia Coli*," *Proc. Natl. Acad. Sci. USA*, vol. 85, p. 5879–5883.

(List continued on next page.)

Primary Examiner—Geetha P. Bansal
(74) Attorney, Agent, or Firm—Lahive & Cockfield, LLP; Jane E. Remillard; Peter W. Dini

(57) ABSTRACT

Disclosed are methods of stimulating in a subject an immune response to an antigen to which the immune response is targeted. This method includes the step of administering to the subject a binding agent which binds a surface receptor of an antigen-presenting cell, in some instances without being blocked substantially by the natural ligand for the surface receptor, and an antigen to which the immune response is targeted, in a physiologically acceptable medium to the subject. Also disclosed are molecular complexes including the binding agent coupled to an antigen.

20 Claims, 4 Drawing Sheets

OTHER PUBLICATIONS

Karpovsky, B., et al., (1984), "Production of Target–Specific Effector Cells Using Hetero–Cross–Linked Aggregates Containing Anti–Target Cell and Anti–Fcγ Receptor Antibodies," *J. Exp. Med.*, vol. 160, pp. 1686–1701.

Kawamura, H., et al., (1986), "Enhancement of Antigenic Potency in Vitro and Immunogenicity in Vivo by Coupling the Antigen to Anti–Immunoglobulin," *J. Immunol.*, vol. 136, No. 1, pp. 58–65.

Köhler, G., and Milstein, C., (1975), "Continuous Cultures of Fused Cells Secreting Antibody of Predefined Specificity," *Nature*, vol. 256, p. 495–497.

Kranz, D., et al., (1981), "Restricted Reassociation of Heavy and Light Chains From Hapten–Specific Monoclonal Antibodies," *Proc. Natl. Acad. Sci. USA*, vol. 78, No. 9, pp. 5807–5811.

Lanzavecchia, A., (1985), "Antigen–specific Interaction Between T and B Cells," *Nature*, vol. 314, pp. 537–539.

Liu, M.A., et al., (1985), "Heteroantibody Duplexes Target Cells for Lysis by Cytotoxic T Lymphocytes," *Proc. Natl. Acad. Sci. USA*, vol. 82, pp. 8648–8652.

Louis, J.A. and Lambert, P.H., (1985), "Making the Immune System Work," *Immunology Today*, vol. 6, No. 9, p. 245.

Manca, F., et al., (1988), "Differential Activation of T Cell Clones Stimulated by Macrophages Exposed to Antigen Complexed with Monoclonal Antibodies," *Immunol.*, vol. 140, No. 9 pp. 2893–2898.

Matsushita, S., et al., (1988), "Characterization of a Human Immunodeficiency Virus Neutralizing Monoclonal Antibody and Mapping of the Neutralizing Epitope," *J. of Virol.*, vol. 62, No. 6, pp. 2107–2114.

Mentzer, S., et al., (1986), "Spontaneous Aggregation as a Mechanism for Human Monocyte Purification," *Cell. Immunol.*, vol. 101, pp. 312–319.

Nair, S., et al., (1992), "Soluble Proteins Delivered to Dendritic Cells Via pH–sensitive Liposomes Induce Primary Cytotoxic T Lymphocyte Responses in Vitro," *J. Exp. Med.*, vol. 175, pp. 609–612.

Parker, D., et al., (1991), "Antigen Presentation in Acquired Immunological Tolerance," *FASEB J.*, vol. 5, pp. 2777–2784.

Partis, M.D., et al., (1983), "Cross–Linking of Protein by ω–Maleimido Alkanoyl N–Hydroxysuccinimido Esters," *J. Protein Chem.*, vol. 2, No. 3 p. 263–277.

Paulus, H., (1985), "Preparation and Biomedical Applications of Bispecific Antibodies," *Behring Inst. Mitt.*, No. 78, pp. 118–132.

Reddy, R., et al., (1992), "In Vivo Cytotoxic T Lymphocyte Induction with Soluble Proteins Administered in Liposomes," *J. Immunol.*, vol. 148, No. 5 pp. 1585–1589.

Schalke, B.C.G., et al., (1985), "Enhanced Activation of a T Cell Line Specific for Acetylcholine Receptor (AChR) by Using Anti–AChR Monoclonal Antibodies Plus Receptors," *J. Immunol.*, vol. 134, No. 6, pp. 3643–3648.

Shen, L., et al., (1986), "Heteroantibody–Mediated Cytotoxicity: Antibody to the High Affinity Fc Receptor For IgG Mediates Cytotoxicity by by Human Monocytes that is Enhanced by Interferon–γ and is not Blocked by Human IgG," *J. Immunol.*, vol. 137, No. 11 pp. 3378–3382.

Skerra, A., et al., (1988), "Assembly of a Functional Immunoglobulin Fv Fragment in *Escherichia Coli*," *Science*, vol. 244, pp. 1038–1041.

Slamon, D., et al., (1989), "Studies of the HER–2/neu Proto–oncogene in Human Breast and Ovarian Cancer," *Science*, vol. 244, p. 707.

Snider, D.P. and Segal, D.M. (1989), "Efficiency of Antigen Presentation After Antigen Targeting to Surface IgD, IgM, MHC, FcγRII, and B220 Molecules on Murine Splenic B Cells," *J. Immunol.*, vol. 143, No. 1 pp. 59–65.

Snider, D.P. et al., (Oct. 22–25, 1989), "Antigen Targeting Using Heteroconjugate Antibodies in Vivo," *Abstract from Meeting in Annapolis*, p. 59.

Snider, D.P. et al., (1990), "Enhanced Antigen Immunogenicity Induced by Bispecific Antibodies," *J. Exp. Med.*, vol. 171, pp. 1957–1963.

Snider, D.P., et al., (1987), "Tageted Antigen Presentation Using Crosslinked Antibody Heteroaggregates," *J. Immunol.*, vol. 139, No. 5 pp. 1609–1616.

Unkeless, J., (1989), "Function and Heterogeneity of Human Fc Receptors for Immunoglobulin G," *J. Clin. Invest.*, vol. 83, p. 355–361.

Van de Winkel, J., et al., (1991), "Biology of Human Immunoglobulin G Fc Receptors," *J. Leukocyte Biol.*, vol. 49, pp. 511–524.

Wagner, E., et al., (1990), "Transferrin–polycation Conjugates as Carriers for DNA Uptake into Cells," *Proc. Natl. Acad. Sci. USA*, vol. 87, pp. 3410–3414.

Waldmann, T., (1991), "Monoclonal Antibodies in Diagnosis and Therapy," *Science*, vol. 252, pp. 1657–1662.

Zanetti, M., (1992), "Antigenized Antibodies," *Nature*, vol. 355, pp. 476–477.

Browning et al. Cell 72:847–856, 1993.*

* cited by examiner

US 6,258,358 B1

TARGETED IMMUNOSTIMULATION WITH BISPECIFIC REAGENTS

REFERENCE TO RELATED APPLICATION

This application is a divisional of patent application Ser. No. 08/249,669, filed May 26, 1994, pending, which is a continuation of patent application Ser. No. 07/874,622, filed Apr. 27, 1992, now abandoned, which is a continuation-in-part of patent application Ser. No. 07/593,083, filed Oct. 5, 1990 (abandoned May 7, 1992), now abandoned. The contents of each of the above applications are hereby incorporated by reference.

BACKGROUND OF THE INVENTION

Antigen molecules are recognized by the immune system after internal processing by antigen-presenting cells, generally mononuclear phagocytic cells such as macrophages and B lymphocytes. In order to present a proteinaceous antigen, the antigen-presenting cell first internalizes the antigen which is then broken down into small peptidic fragments by enzymes contained in vesicles in the cytoplasm of the antigen-presenting cells. After fragmentation, the peptides are linked to cellular major histocompatibility complex (MHC) molecules and presented on the presenting cell's surface to the immune system. Peptides presented in this way are recognized by the T-cell receptor which engages T-lymphocytes into the immune response against this antigen. This antigen presentation also stimulates the B lymphocytes for specific antibody production.

Complexes of antibody and antigen have been used to stimulate an immune response against the antigen. Antigen uptake through antigen-antibody complexes bound to Fc receptors for IgG (FcγR) increases the efficiency of antigen presentation and thereby antigen-specific T-cell activation by human and mouse macrophages, (Celis et al (1984) *Science* 2:297–299; Chang (1985) *Immunol. Today* 6:245–259; Manca et al. (1988) *Immunol.* 140:2893–2898; Schalke et al. (1985) *J. Immunol.* 13:3643–3648; and Snider et al (1987) *J. Immunol.* 1:1609–1616). The binding of these complexes to FcγR is mediated by the Fc region of the antibody. This binding is susceptible to inhibition by physiological concentrations of IgG.

SUMMARY OF THE INVENTION

This invention pertains to a binding agent which binds a surface receptor of an antigen-presenting cell in some instances without being blocked substantially by the natural ligand for the receptor and which binds the antigen.

In one aspect of the invention, the binding agent employed is bispecific agent such as a heteroantibody, bispecific antibody, or other bispecific molecule having a binding specificity for the antigen and a binding specificity for a surface receptor of an antigen-presenting cell, such as a mononuclear phagocyte (e.g., a macrophage).

As used herein, the term "heteroantibody" refers to a conjugate of at least the antibody binding sites of two or more antibody molecules of different specificities.

An "antibody binding site" is that portion of the antibody molecule which binds a particular antigenic site. This antibody binding site includes an immunoglobulin variable domain that comprises three hypervariable regions flanked by four relatively conserved framework regions. The hypervariable regions are believed to be responsible for the binding specificity of individual antibodies.

The term "bispecific antibody" refers to a single, divalent antibody which has two different antigen binding sites (variable regions).

A "bispecific molecule" is one which has two different binding specificities and which can be bound to two different molecules or two different sites on a molecule concurrently.

The bispecific binding agent binds the cellular receptor, such as an Fc receptor, and targets the antigen to the cell. In some embodiments, this bispecific binding agent binds the cellular receptor without substantially being blocked by the natural ligand for the receptor. In a preferred embodiment, the bispecific binding agent specifically binds an Fc receptor of an antigen-presenting cell for immunoglobulin G (IgG) without being blocked by IgG. Preferred binding agents are specific for FcγRI, FcγRII, and FcγRIII. In a particularly preferred embodiment, the agent specifically binds the high affinity Fc receptor for immunoglobulin G (FcγRI) on macrophages.

In another aspect of the invention, a preferred binding agent is an antibody or binding fragment thereof which includes one or more complementarity determining regions.

As used herein, "complementarity determining region" includes one hypervariable region of an immunoglobulin molecule and selected amino acids disposed in the framework regions which flank that particular hypervariable region in an immunoglobulin molecule.

In some aspects of the invention, the binding agent includes at least two antibody binding fragments linked together by chemical methods or genetically linked via recombinant DNA techniques. One preferable binding agent is a Fab—Fab conjugate, wherein the first Fab binds the high affinity Fc receptor as described above, and the second Fab binds the antigen.

The binding agent of the invention is used to stimulate in a subject an immune response to an antigen. In this method a binding agent and an antigen are provided and administered in a pharmacologically acceptable medium to the subject. The binding agent targets the antigen to the antigen-presenting cell in the subject.

The antigen to be targeted can be derived from a foreign pathogen such as a viral, bacterial, or parasite antigen, or it can be derived from endogenous diseased host cells such as tumor associated antigens on tumor cells. Preferred binding agents include antibodies specific for antigens derived from hepatitis virus such as the hepatitis surface antigen, or an HIV antigen. Other binding agents bind an epitope on bee venom, pollen, or dust mite antigen.

Generally, the antigen is administered as a preformed, chemically coupled complex with the binding agent. Alternatively the antigen is incorporated into the binding agent through recombinant DNA techniques to create a genetic hybrid that codes for a fusion product including the binding agent and antigen. In some cases, however, the antigen and the bispecific binding agent are administered separately or the binding agent may be administered alone.

In another embodiment of the invention, the antigen is directly bound to a receptor-binding agent to create bispecific molecules (e.g., receptor-specific antigens). For example, the antigen can be covalently coupled to an antibody which binds the Fc receptor without being blocked by IgG.

The binding agent which binds an Fc receptor may also be incorporated into a lipid emulsion or the outer layer of a liposome which contains the antigen. Preferably, the binding agent is an antibody which recognizes the FcγRI receptor. An additional aspect of the invention is a vaccine including the molecular complex of the invention in a pharmacologically acceptable medium.

The compositions of this invention can be used to treat or prevent infectious diseases such as hepatitis B, to neutralize the acute phase of an infection by a pathogenic organism, to stimulate the immune system in instances of chronic infection of such an organism, to deplete antigen in the circulation of a subject, and to treat tumors.

This invention also relates to methods and compositions used to induce IgG responses against allergens to effect tolerance in the case of IgE-mediated type I hypersensitivity, and to induce a state of T cell tolerance to allergens which would interfere with the development of IgE mediated responses. In these methods a molecular complex is administered which consists of an allergen which binds to IgE on mast cells and basophils, complexed to a heteroantibody that binds the high affinity Fc receptor without being blocked by IgG binding to the receptor. Enough of the complex is administered to the circulation of a subject such that an immune response is induced, which may include the production of allergen-specific IgG, thereby inhibiting the binding of the allergen to IgE on mast cells and basophils. Alternatively, the administration of the complex induces a state of T cell tolerance to the allergen by binding to naive B cells, thereby interfering with an IgE-mediated type I reaction.

BRIEF DESCRIPTION OF THE DRAWINGS

The invention itself can be more fully understood from the following description when read together with the accompanying drawings in which:

FIG. 1A shows T cell proliferation in response to monoclonal antibody-tetanus toxoid (mAb-TT) conjugates; FIG. 1B shows T cell proliferation in response to HIgG anti-TT; and FIG. 1C shows T cell proliferation in response to mAb-TT conjugate as compared to that of $IgG_1$ anti-TT mAb+TT and TT alone;

FIG. 2A shows that an anti-FcγRI mAb (197) blocks $HIgG_1$ and anti-FcγRI (22.2)-TT-enhanced antigen presentation; while anti-FcγRII (IV.3) and anti-FcγRIII (368) mAbs do not. FIG. 2B shows that mAb 197 does not block enhanced T cell proliferation by anti-FcγRIII (368)-TT conjugates; FIG. 3A is a graph showing the amount of $HIgG_1$ required to saturate FcγRI at 4° C. and at 37° C.; and FIG. 3B is a bar graph showing the effect of varying concentrations of $HIgG_1$ on anti-FcγRI (22.2)-TT-enhanced antigen presentation, as measured by T cell proliferation.

DETAILED DESCRIPTION OF THE INVENTION

Figure 1A:
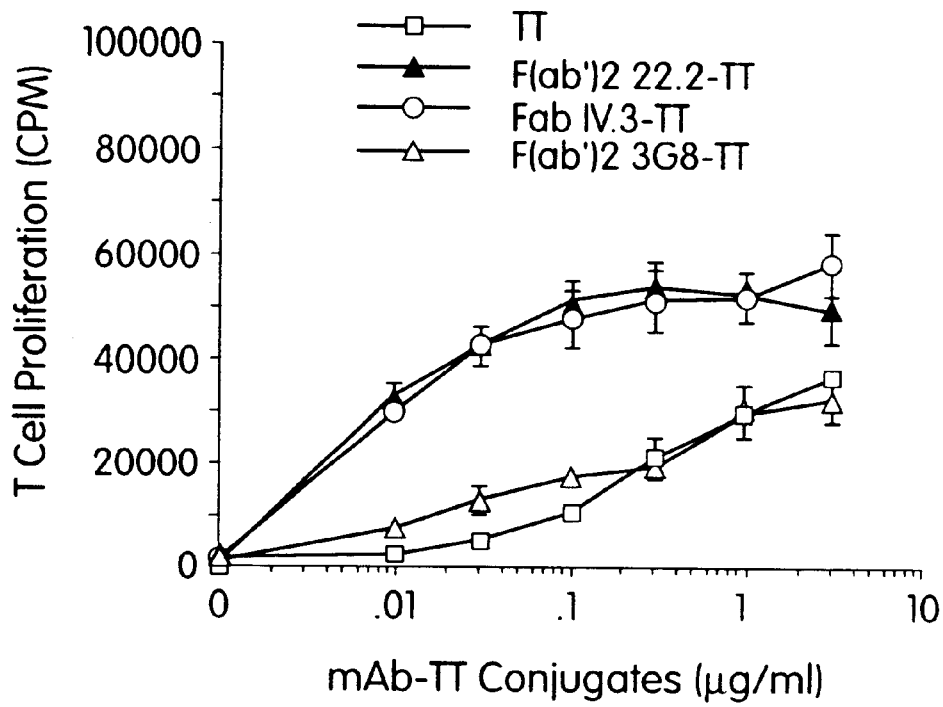
FIGS. 1A, 1B, and 1C are graphs demonstrating the enhancement of antigen presentation by monocytes to T cells using anti-FcγR-Ag conjugates or human $IgG_1$ ($HIgG_1$) anti-Ag mAb.

An optimal antibody response to a thymus-dependent antigen requires that the B cell obtain help from a CD4+ helper T cell. The B cell is uniquely designed to accomplish this in that it contains antigen-specific immunoglobulin on its surface which allows it to bind, internalize and process antigen for presentation very efficiently. Other antigen presenting cells, such as the macrophage and dendritic cell, lack antigen-specific receptors, and therefore also lack this highly efficient mechanism for processing and presenting antigen. However, the apparent requirement for adjuvants when administering vaccines suggests a need for an antigen presenting cell in addition to the B cell. Also, it appears that antigen presentation by resting B cells to resting T cells does not lead to a T cell activation, but rather to T cell tolerance (Eynon et al. (1992) *J. Exp. Med.* 175:131). This is due to the failure of the resting B cell to deliver all the signals required for activation of the resting T cell. On the other hand, it appears that induction of T cell tolerance by the resting B cell could be averted if the resting T cell first responds to antigen on the antigen presenting cell such as the macrophage or dendritic cell (Parker et al. (1991) *FASEB J.* 5:2777). This implies that in the naive individual, the resting T cell must first interact with a macrophage or dendritic cell before interacting with the resting B cell.

These considerations have lead to the conclusion that the optimal immunogen requires two major components: antigen which can be recognized by the antigen-specific B cell; and a component which directs antigen for efficient processing and presentation to an antigen presenting cell other than the resting B cell (Parker et al., ibid.; Germain (1991) *Nature* 3:605). Attaching antigens to anti-Fc receptor antibodies satisfies these criteria since antigen directed to Fc receptors on the macrophage enhances antigen presentation at least 100 fold (*Immunol. Today* (1985) 6:245). Studies in vivo support the efficacy of such a vaccine. For example, a substantial increase in antibody production has been observed following immunization of mice with bispecific antibody which directed antigen to MHC class II or FcγRII (Snider et al. (1990) (*J. Exp. Med.* 121:1957–1963). In addition, the requirement for adjuvant was eliminated. The ability to use substantially lower doses of immunogens is especially valuable when administering immunogens such as allergens that are potentially toxic at higher doses. Tolerance against some allergens can be obtained by repeated low dose administration of the allergen. Tolerance may result from the production of IgG against the allergen, which competes with allergen-specific IgE, removing the allergen so that it will not interact with IgE-coated mast cells. Allergen-anti-Fc receptor conjugates have the potential to both reduce the amount of allergen administered, thereby further reducing toxicity, and, at the same time, increase the production of allergen-specific IgG.

To construct an immunogen for human use which would satisfy the above criteria, the observation that antigen-antibody complexes can significantly enhance antigen presentation was expanded. When antigen-antibody complexes bind to FcγR on the monocyte or macrophage, the antigen is internalized and its subsequent presentation and thus T cell activation, is dramatically enhanced in vitro (Chang (1985) *Immunol. Today* 6:245), decreasing the antigen concentration required for T cell activation by 10 to 100-fold. The data presented here demonstrate the potential for using FcγR-targeted immunogens as vaccines and show that all three Fcγ receptors function to enhance antigen presentation.

In the method of this invention, an antigen is targeted to an antigen-presenting cell to enhance the processes of internalization and presentation by these cells, and ultimately, to stimulate an immune response therein.

In one embodiment of the invention, a bispecific binding reagent is employed to target the antigen to the cell. The bispecific binding agent specifically binds the antigen (either directly, to an epitope of the antigen, or indirectly, to an epitope attached to the antigen) and, at the same time, binds a surface receptor of an antigen-presenting cell which can internalize antigen for processing and presentation. The receptor-binding component of the bispecific binding agent (and thus the bispecific binding agent, itself) binds the receptor of the antigen-presenting cell. In some instances, binding of the agent occurs without the agent substantially being blocked by the natural ligand for the receptor. As a result, targeting of the antigen to the receptor will not be prevented by physiological levels of the ligand and the targeted receptor will remain capable of binding the ligand and functioning.

The preferred surface receptors of antigen-presenting cells for targeting are the receptors for the Fc region of IgG (FcγR). These receptors mediate internalization of antibody-complexed antigens. The Fc receptors include FcγRI, FcγRII, and FcγRIII. The most preferred target is the high affinity Fc receptor (FcγRI).

As described in more detail below, the bispecific binding agents are generally made of antibodies, antibody fragments, or analogs of antibodies containing at least one complementarity determining region derived from an antibody variable region.

Antibodies that bind to Fc receptors on antigen-presenting cells can be produced by conventional monoclonal antibody methodology e.g., the standard somatic cell hybridization technique of Kohler and Milstein (*Nature (*1975) 256:495). Although somatic cell hybridization procedures are preferred, in principle, other techniques for producing monoclonal antibodies can be employed e.g., viral or oncogenic transformation of B lymphocytes.

In general, an animal is immunized with an FcγR-bearing cell, a receptor-bearing portion thereof, or the Fc receptor molecule in purified or partially purified form. Antibodies are selected which bind an epitope of the FcγR which is located outside of the ligand (i.e., Fc) binding domain of the receptor. This binding is not inhibited by IgG and, in turn, does not inhibit the binding of IgG and the function of the Fc receptor.

The production and characterization of monoclonal antibodies which bind FcγRI without being blocked by human IgG are described by Fanger et al. in PCT application WO 88/00052 and in U.S. Pat. No. 4,954,617, the teachings of which are incorporated by reference herein. These antibodies bind to an epitope of FcγRI which is distinct from the Fc binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, Rockville, Md., ATCC No. HB9469.

The bispecific binding agent for targeting the antigen can be a heteroantibody, a bispecific antibody, a bispecific molecule, or an analog of any of these agents. Bispecific antibodies are single, divalent antibodies which have two different antigen binding sites (variable regions). In the bispecific antibodies of this invention, one of the antigen binding sites is specific for the receptor of the antigen-presenting cell and has the characteristics set forth above, and the other binding site is specific for the antigen to be targeted to the antigen-presenting cell. These antibodies can be produced by chemical techniques (see e.g., Kranz et al. (1981) *Proc. Natl. Acad. Sci. USA* 78:5807), by "polydoma" techniques (See U.S. Pat. No. 4,474,893), or by recombinant DNA techniques.

The heteroantibodies of the invention are two or more antibodies or antibody-binding fragments (Fv, Fab, Fab' or $F(ab')_2$) of different binding specificity linked together. Heteroantibodies comprise a first antibody (or antigen-binding fragment thereof) specific for the receptor of the antigen-presenting cell, coupled to a second antibody (or antigen-binding fragment thereof) specific for the antigen to be targeted.

Heteroantibodies can be prepared by conjugating together two or more antibodies or antibody fragments. Preferred heteroantibodies are comprised of crosslinked Fab fragments (Fab—Fab). A variety of coupling or crosslinking agents can be used to conjugate the antibodies. Examples are protein A, carboimide, N-succinimidyl-S-acetyl-thioacetate (SATA) and N-succinimidyl-3-(2-pyridyldithio) propionate (SPDP). See e.g., Karpovsky et al. (1984) *J. Exp. Med,* 16:1686; Liu, M. A. et al. (1985) *Proc. Natl. Acad. Sci. USA* 82:8648. Other methods include those described by Paulus (*Behring Inst. Mitt.* (1985) No. 78, 118–132); Brennan et al. (*Science* (1985) 22:81–83), and Glennie et al. (*J. Immunol.* (1987) 1:2367–2375).

Bispecific binding agents can also be prepared via recombinant DNA techniques from single chain antibodies. See e.g., Huston et al. (1988) *Proc. Natl. Acad. Sci. USA* 85:5879; Skerra et al. (1988) *Science* 240:1038. These are analogs of antibody variable regions produced as a single polypeptide chain. To form the bispecific binding agent, the single chain antibodies may be coupled together chemically or by genetic engineering methods.

As used herein, the term "antigen" means any natural or synthetic immunogenic substance, a fragment or portion of an immunogenic substance, a peptidic epitope, or a hapten. Suitable antibodies against wide variety of antigens for construction of the bispecific binding agents are available or can be readily made by standard techniques.

One type of antigen to which a bispecific binding agent (such as an antibody) can be produced is an allergen. Many allergens are found in airborne pollens of ragweed, grasses, or trees, or in fungi, animals, house dust, or foods. As a class, they are relatively resistant to proteolytic digestion. Preferable allergens are those which bind to IgE on mast cells and basophils, thereby causing a type I anaphylazis hypersensitivity reaction. When the second specificity of the bispecific binding agent is for an epitope of the high affinity Fc receptor that is outside the ligand binding domain for IgG, this bispecific binding agent can decrease hypersensitivity in a subject. This is accomplished when the bispecific binding agent competes for an IgE-binding allergen before the allergen binds to IgE on a mast cell or basophil, thereby reducing the possibility of a type I hypersensitivity reaction. In addition, as a result of directing allergen to FcγR, a state of T cell tolerance to the allergen may be induced which interferes with IgE-mediated type I reactions. Tolerance can be accomplished by inducing IgG which competes with IgE for binding to allergen using doses of allergen substantially lower than those currently used.

In some cases, it may be desirable to couple a substance which is weakly antigenic or nonantigenic in its own right (such as a hapten) to a carrier molecule, such as a large immunogenic protein (e.g., a bacterial toxin) for administration. In these instances, the bispecific binding reagent can be made to bind an epitope of the carrier to which the substance is coupled, rather than an epitope of the substance itself.

In another embodiment of the invention, the antigen can be coupled directly to the binding agent for the receptor. In these instances, the antibody itself can serve as the carrier protein. For example, an antigen can be coupled to an antibody, or fragment thereof, specific for an Fc receptor of an antigen-presenting cell. Proteinaceous antigens can be biochemically coupled by the methods described above or by other methods known by those with skill in the art. Alternatively, a fusion protein may be produced by the expression of an immunoglobulin gene genetically engineered to include a gene encoding the antigen (Zanetti (1992) *Nature* 35:476–477). Such methods are described in detail in Sambrook et al. (*Molecular Cloning, A Laboratory Manual* (Second Edition), Cold Spring Harbor Press, 1989), herein incorporated by reference.

In another aspect of the invention, the antigen is targeted to a cell via a carrier which contains antigen. Useful carriers include lipid emulsions or synthetic lipid vesicles, i.e., liposomes, having incorporated into the outer layer of the liposome the binding agent of the invention (Nair et al. (1992) *J. Exp. Med.* 1:609–612; and Reddy et al. (1992) *J. Immunol.* 148:1585–1589). The allergen may be encapsulated within the internal aqueous space, or entrapped within the lipid bilayer(s), of the liposome. Antigen-carrying liposomes can be fabricated according to procedures known in the art, such as those described by Bangham et al. (*J. Mol. Biol.* (1965) 12:238–252), and by Papahadjopoulos et al. (U.S. Pat. No. 4,241,046), herein incorporated by reference. In other embodiments of the invention, the binding agent is incorporated into a lipid emulsion or the outer layer of a liposome containing antigen.

Alternatively, the binding agent may be incorporated into a biodegradable hydrogel containing an allergen.

The antigen targeted by the methods of this invention can be soluble or particulate; it may carry B cell epitopes, T cell epitopes or both. The antigen can be bacterial, viral or parasitic in origin. Often, the antigen will comprise a component of the surface structure of a pathogenic organism. For example, the antigen can comprise a viral surface structure such as an envelope glycoprotein of human immunodeficiency virus (HIV) or the surface antigen of hepatitis virus. In addition, the antigen can be associated with a diseased cell, such as a tumor cell, against which an immune response may be raised for treatment of the disease. The antigen can comprise a tumor-specific or tumor-associated antigen, such as the Her-2/neu proto-oncogene product which is expressed on human breast and ovarian cancer cells (Slamon et al. (1989) *Science* 244:707).

Targeted immunostimulation can be performed in vitro or in vivo. The bispecific binding agent can be used to target antigen to antigen-presenting cells in culture. Immunocompetent cells are separated and purified from patient blood. The cells are exposed to the antigen and the binding agent. Targeted antigen-presenting cells will process the antigen and present fragments on their surface. After stimulation, the cells can be returned to the patient.

To elicit an immune response in vivo, the antigen can be administered to a subject in conjunction with the binding agent. Although in some circumstances the two may be administered separately, typically, they are administered as a preformed immunochemical complex. The complex is formed by incubating the antigen and the bispecific binding agent at a desired molar ratio under conditions which permit binding of the two species. For example, the antigen and the bispecific binding reagent can be incubated in saline solution at 37° C. In some embodiments, for therapy of a pre-existing condition, the bispecific binding agent may be given without accompanying antigen.

The complex is administered in a pharmacologically acceptable solution at a dosage which will evoke an immune response against the antigen. The optimum dose of antigen, as well as the molar ratio of antigen and binding agent, may vary dependent upon factors such as the type of antigen, the immune status of the host, the type of infection or other disease being treated, etc. In most cases, the dose of antigen required to elicit an immune response (as determined by any standard method for assessment of immune response) should be lower than that which would be required if the antigen were given alone or as a complex with a monospecific antibody for the antigen (Snider et al., ibid.). Of course, the dose should also be lower than that which elicits an allergic response.

The method of this invention can be used to enhance or reinforce the immune response to an antigen. For example, the method is valuable for the treatment of chronic infections, such as hepatitis and AIDS, where the unaided immune system is unable to overcome the infection. It can also be used in the treatment of the acute stages of infection when reinforcement of immune response against the invading organism may be necessary.

The method can be used to reduce the dose of antigen required to obtain a protective or therapeutic immune response or in instances when the host does not respond or responds minimally to the antigen. Although generally desirable, the lowering of effective dose can be especially desirable when the antigen is toxic to the host such as is the case for allergies.

The method of targeted immunostimulation can also be used in disease therapy. For example, the bispecific binding agent can be used to target a tumor-associated (or tumor-specific) antigen to an antigen-presenting cell in order to cause or to enhance an immune response against the tumor.

The invention is illustrated further by the following nonlimiting exemplification.

EXAMPLE 1

Anti-Human Erythrocyte, Anti-FcγRI Heteroantibody

A. Procedure

A bispecific heteroantibody was prepared from a monoclonal antibody against human erythrocytes (mono-D, a human anti-RhD antibody) and anti-FcγRI antibody 32, by a protocol previously described. Shen et al. (*J. Immunol.* (1986) 137:3378). Briefly, human erythrocytes were washed three times in buffer solution and then incubated for 60 minutes at 37° C. in solution of the heteroantibody. After the incubation and three washings, erythrocytes coated with heteroantibody were diluted at $5 \times 10^7$ cells per millimeter in Hank's buffer and then incubated with adherent monocytes (macrophages) at the ratio of 100:1 for one hour at 37° C. Cells were then washed in phosphate buffered saline (PBS), fixed for one minute in ethanol and stained with Giemsa for observation through a light microscope.

B. Results

Internalization of erythrocytes was easily observed as unstained spheres in the macrophage cytoplasm. The number of macrophages that internalized at least one erythrocyte were counted. This experiment was repeated numerous times with and without the heteroantibody present. In each experiment, no erythrocyte internalization was observed in macrophages which were incubated with erythrocytes in the absence of the heteroantibody.

In addition, experiments were performed after treatment of adherent monocytes (macrophages) with various concentrations of interferon-gamma which is known to increase the number of FcγRI receptors on the macrophage surface (Guyre et al. (1988) *J. Steroid Biochem.* 3:1–6). As shown in TABLE 1 below, the number of macrophages that internalized erythrocytes increased in a direct relation to the concentration of interferon-gamma.

TABLE 1

| gamma interferon concentration ($\mu$g/ml) | % macrophages having internalized at least one erythrocyte |
| --- | --- |
| 1000 | 40 |
| 100 | 25 |
| 10 | 6 |

These data show that the heteroantibody can trigger Internalization of antigen by macrophages.

EXAMPLE 2

Enhancement of Antigen Presentation by Anti-Fc$\gamma$R-Ag and HIgG$_1$

A. Procedure

1. Cell Preparation

Monocytes used in the assay were purified from peripheral blood using techniques which minimize contamination with endotoxins (Menzer et al. (1986) Cell. Immunol. 101:312–319). Monocyte purity was approximately 85–95% as judged by morphology and expression of the CD14 surface antigen.

Cd4+ T cells used in the assay were isolated following a primary stimulation of donor mononuclear cells with tetanus toxin. Briefly, mononuclear cells were isolated from peripheral blood using Ficoll-Hypaque (Winthrop Pharmaceuticals, New York, N.Y.). 30×10$^6$ mononuclear cells were stimulated in 50 ml of AIM V medium (Gibco, Grand Island, N.Y.) with 5 $\mu$g/ml tetanus toxin (Accurate Chemical Co., Westbury, N.Y.).

AIM V is a defined (serum free) medium for the growth of human cells. The use of AIM V reduces non-specific T cell responses while maintaining Ag-specific responses equal to those observed with other media tested. This medium allows more definitive studies of Fc receptor-enhanced antigen presentation in vitro. If antigen is directed to Fc receptors using monoclonal antibodies that bind to Fc receptors regardless of the presence of human IgG, this medium is not a requirement to see enhanced antigen presentation.

After three days at 37° C., unbound cells were removed by washing flasks 3× with Hepes-buffered RPMI-1640 (HRPMI). 40 ml of AIM V were added back to each flask along with 10 units/ml recombinant human interleukin IL-2 (Immunex, Seattle, Wash.) and 2.5% autologous serum. After 10 to 14 days total incubation time, T cells were harvested and dead cells were pelleted through Ficoll Hypaque, yielding a highly enriched population (90–95%) of CD4+, antigen-specific T cells. Use of this primed polyclonal population of T cells minimizes non-specific responses and xenogenic responses to mouse immunoglobulin, and reduces the potential (which would exist using T cell clones) that T cell responses will be sensitive to tetanus toxin modification as a result of monoclonal antibody-tetanus toxin (mAb-TT) conjugation or antibody binding to tetanus toxin.

2. Antibody Preparation

The mAb-TT conjugates used in the assay were made by inducing sulfhydryl groups on TT using N-succinimidyl-S-acetyl-thioacetate, and linking TT to sulfosuccinimidyl 4-(N maleimidomethyl) cyclohexane-I-carboxylate treated (Fab')$_2$ mAb at a 1:1 molar ratio of TT:mAb (Partis et al. (1983) J. Protein Chem. 2:263. HIgG anti-TT was produced by a hybridoma (SA13) which was obtained from ATCC. The IgG anti-TT mAb was purified with DEAE HPLC. This isotype of the IgG anti-TT mAb was determined by ELISA to be IgG$_1$.

3. Antigen Presentation Assays

Antigen presentation assays were done as follows: 5×10$^4$ T cells and 5×10$^4$ monocytes, each in 50 $\mu$l of AIM V medium, were added to wells of a 96 well microtiter plate. Monocytes were treated with mitomycin C before addition to wells to prevent proliferation of the antigen presenting cells and the few contaminating lymphocytes. The volume of AIM V/well was then increased such that once mAb and/or TT or mAb-TT conjugates were added, the final volume was 200 $\mu$l. Monoclonal antibody [(Fab')$_2$ anti-Fc$\gamma$RI (22.2), Fab anti-Fc$\gamma$RII (IV.3), (Fab')$_2$ anti-Fc$\gamma$RIII (3G8)]-TT conjugates, or TT with or without whole HIgG$_1$ anti-TT, was added. Monoclonal antibody 22 (mAb 22) is specific for the high affinity Fc$\gamma$ receptor, and its binding to the receptor is not blocked by IgG Fc (see U.S. Pat. No. 4,954,617). mAb IV.3 and 3G8 are specific for the ligand binding domains of Fc$\gamma$RII and Fc$\gamma$RIII (Van de Winkel et al. (1991) J. Leukocyte Biol. 11:511). Following addition of cells and antigen to wells, plates were incubated for 72 hours (h) at 37° C. in a CO$_2$ incubator. After 72 h, [$^3$H]-thymidine was added in order to detect T cell proliferation, according to the method of Lanzavecchia (Nature (1985) 31:537).

B. Results

To determine which Fc$\gamma$R types best participate in enhancing antigen presentation, two approaches were used. In the first, tetanus toxin was attached to (Fab')$_2$ anti-Fc$\gamma$RI, Fab anti-Fc$\gamma$RII, or (Fab')$_2$ anti-Fc$\gamma$RIII monoclonal antibodies (mAb). In the second approach, TT plus whole monomeric human IgG$_1$ (HIgG$_1$) anti-TT was added to cultures. It was expected that a HIgG$_1$-dependent response would involve Fc$\gamma$RI, since human Fc$\gamma$RI binds monomeric HIgG (Unkeless (1989) J. Clin. Invest. 83:355). In both systems, responses were compared to those of tetanus toxin alone.

Figure 1B:
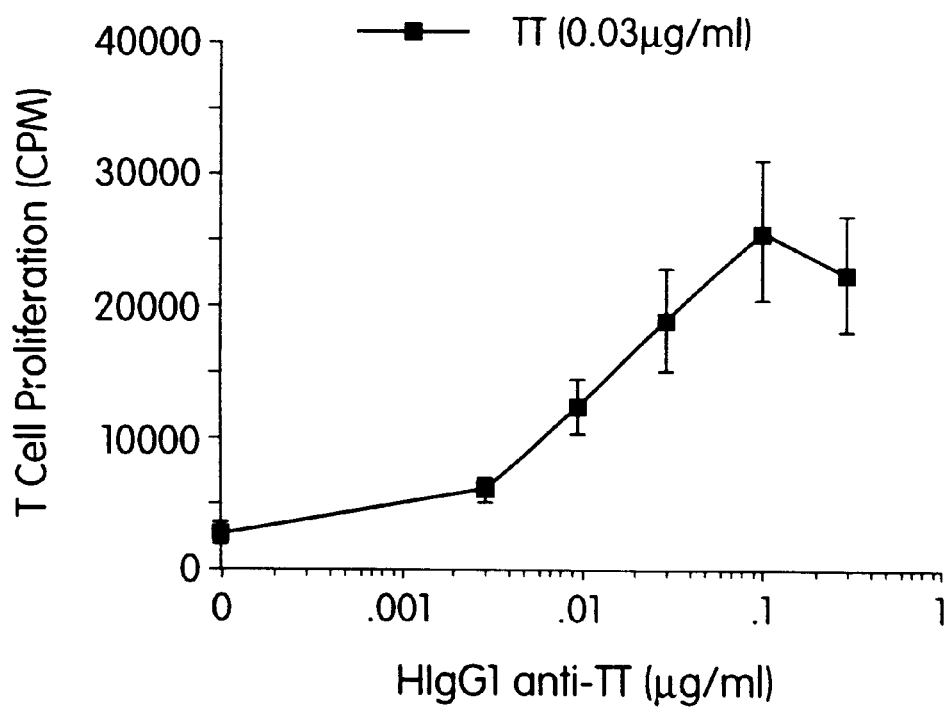

Both methods produced enhanced presentation of tetanus toxin (FIGS. 1A, 1B), and all three human Fc$\gamma$R types participate (FIG. 1A). Anti-Fc$\gamma$RI-TT and anti-Fc$\gamma$RII-TT conjugates enhanced antigen presentation the greatest (100-fold) as compared to anti-Fc$\gamma$RIII-TT conjugates which enhanced antigen presentation the least (10-fold). This difference is likely due to the smaller percentage (10 to 15%) of monocytes which express Fc$\gamma$RIII on their surface, as opposed to those expressing Fc$\gamma$RI and Fc$\gamma$RII (100%) (Van de Winkel et al. (1991) J. Leukocyte Biol. 49:511). In addition, the anti-Fc$\gamma$RI-TT conjugate was consistently more effective than the HIgG, anti-TT+TT complex (FIG. 1C).

Figure 1C:
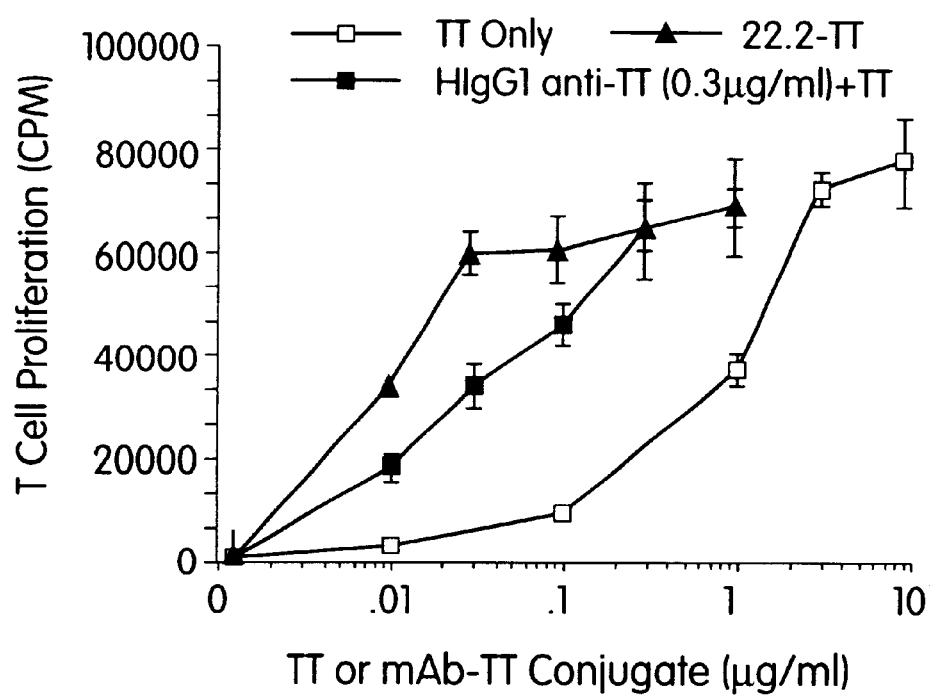

In three separate, but similar experiments, including the experiment depicted in FIG. 1C, enhancement of the response with the anti-Fc$\gamma$RI-TT conjugate was consistently 100 to 150-fold, but only 30 to 50-fold for the HIgG$_1$-anti-TT+TT complex. A possible explanation for this observation is the following. Analysis by high pressure liquid chromatography (HPLC) indicates that aggregates of tetanus toxin were present in all tetanus toxin preparations. Therefore, the presence of large IgG$_1$-anti-TT+TT complexes might result in some tetanus toxin enhancement through the less effective Fc$\gamma$RIII.

EXAMPLE 3

HIgG$_1$ Targeting of Enhanced Antigen Presentation to Human Fc$\gamma$RI

A. Procedure

Experiments were done as in EXAMPLE 1, except that the blocking anti-Fc$\gamma$R mAb listed in EXAMPLE 1 or whole IgG$_{2a}$ anti-Fc$\gamma$RI (197) were added to wells at 37° C. for 2 h prior to addition of IgG1anti-TT+TT, anti-Fc$\gamma$RI-TT conjugate, or TT, alone. Monoclonal Ab 197 is a mouse IgG$_{2a}$ which binds to human Fc$\gamma$RI by both its Fc and Fab binding domains (Guyre et al. (1989) J. Immunol., 143:1650).

B. Results

Figure 2A:
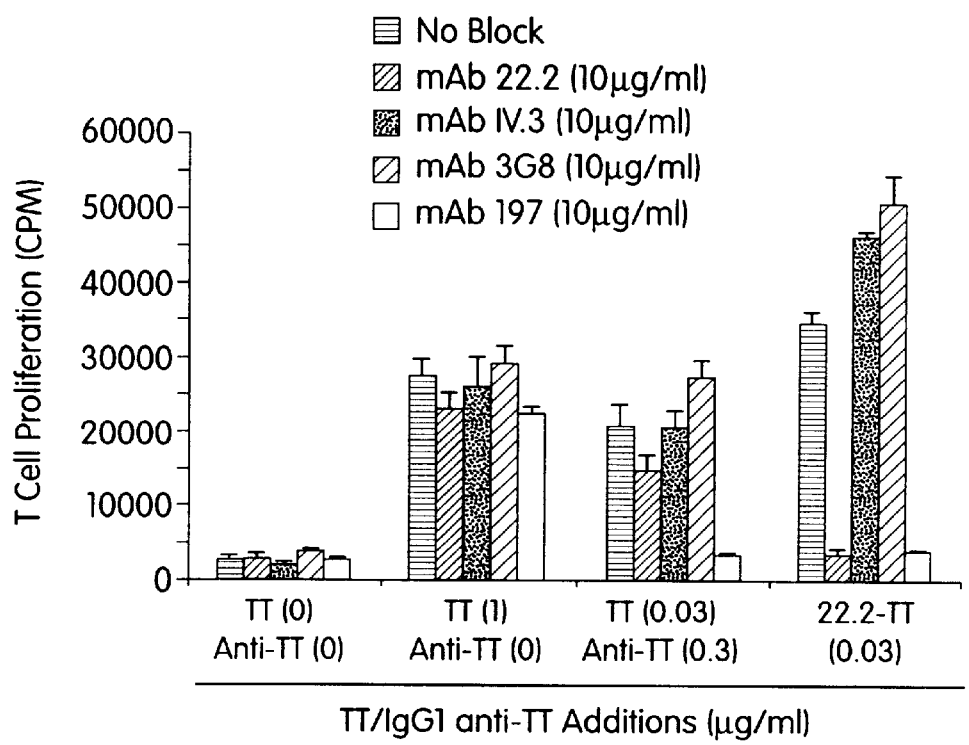
FIGS. 2A and 2B are bar graphs demonstrating the ability of the dominant HIgG isotype, $HIgG_1$, and anti-FcγRI (22.2)-TT to target enhanced antigen presentation to human FcγRI.
Figure 2B:
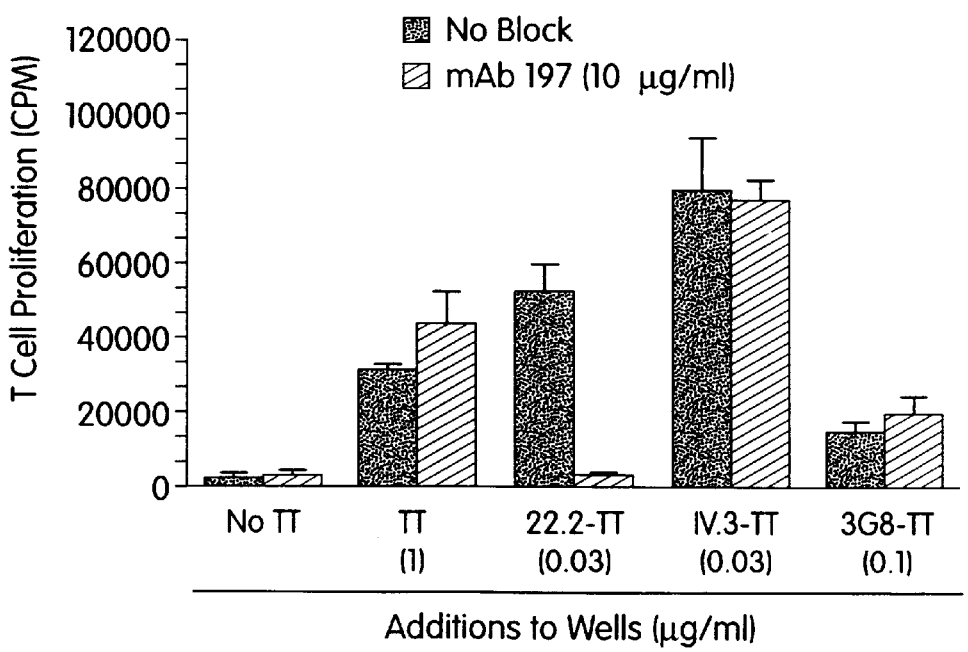

To confirm the specificity of the $IgG_1$ anti-TT enhancement for FcγRI, enhancement was eliminated with blocking concentrations of anti-FcγR mAb against each FcγR type. The results are shown in FIGS. 2A and 2B, where T cell proliferation is expressed as the mean counts/min (CPM) of three replicates±standard deviation (SD). $(Fab')_2$ mAb alone or added in combination with tetanus toxin had no effect on T cell proliferation (FIG. 2A). Only the anti-FcγRI mAb 197 blocked $IgG_1$ anti-TT-enhanced antigen presentation (FIG. 2A). Monoclonal Ab 197 binds to FcγRI by both its Fc and Fab domains (Guyre et al. (1989) *J. Immunol.* 14:1650). At 37° C., this results in crosslinking and capping of FcγRI such that it is no longer available for ligand binding (Partis et al. (1983) *J. Protein Chem.* 2:263). A role for the Fc domain of mAb 197 in blocking FcγRII or FcγRIII enhanced Ag presentation was excluded by showing that mAb 197 blocks enhanced presentation with anti-FcγRI-TT conjugates, but does not block enhanced presentation using anti-FcγRII-TT and anti-FcγRIII-TT conjugates (FIG. 2B).

EXAMPLE 4

Blockage Inhibition of FcγRI-Enhanced Antigen Presentation by HIgG

A. Procedure

Flow-cytometric analysis was performed essentially as described by Gosselin et al. (*J. Immunol.* (1990) 144:1817) to determine the amount of $HIgG_1$ required to saturate FcγRI. Briefly, cells were diluted in AIM V. To individual wells of a 96 well pate, 30 µl of $5\times10^4$ monocytes from the same donor as in EXAMPLE 2 were added. This was followed by 30 µl of AIM V containing 2×(twice concentrated) $HIgG_1$. $HIgG_1$ was purified from the serum of a myeloma patient using a sizing column and HPLC. The plates were then incubated for 2 h at 4° C. Plates were centrifuged, the supernatants discarded, and the cells washed 3× with PBS/BSA at 4° C. Cells were then incubated for 1.5 h with 40 µl/well of FITC-labeled $(Fab')_2$ goat anti-HIgG (Caltas, San Francisco, Calif.), followed by 3 washes with PBS/BSA and resuspension in PBS/BSA containing 1% formaldehyde (Kodak, Rochester, N.Y.). Similar studies were done on monocytes incubated for 1 h at 37° C. in the presence of 0.1% sodium azide (Sigma, St. Louis, Mo.).

Another assay was done as described in EXAMPLE 1 except that $HIgG_1$ was added first on ice followed by 22.2-TT conjugates or $HIgG_1$ anti-TT+TT.

B. Results

Figure 3A:
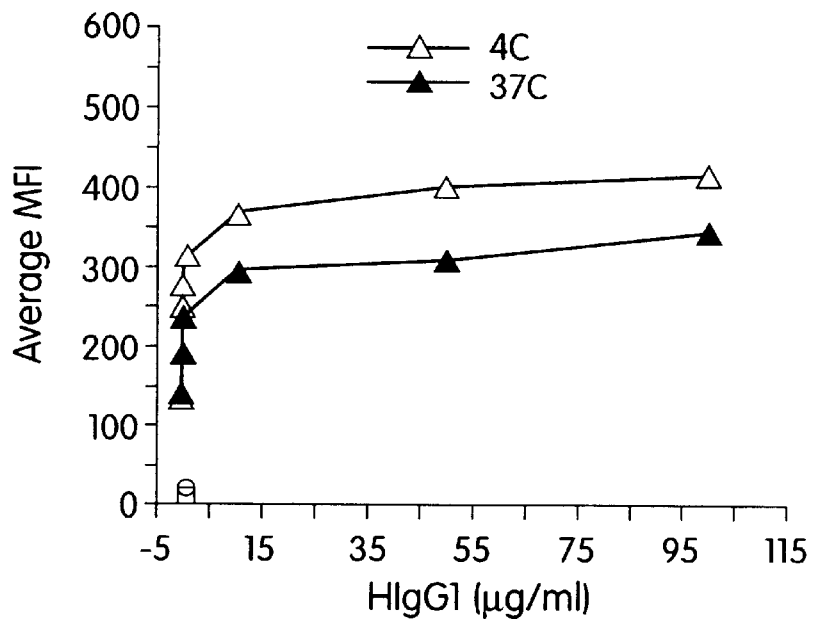
FIGS. 3A and 3B show the ability of anti-FcγRI-(22.2)-TT to overcome blocking of FcγRI-enhanced antigen presentation by HIgG.
Figure 3B:
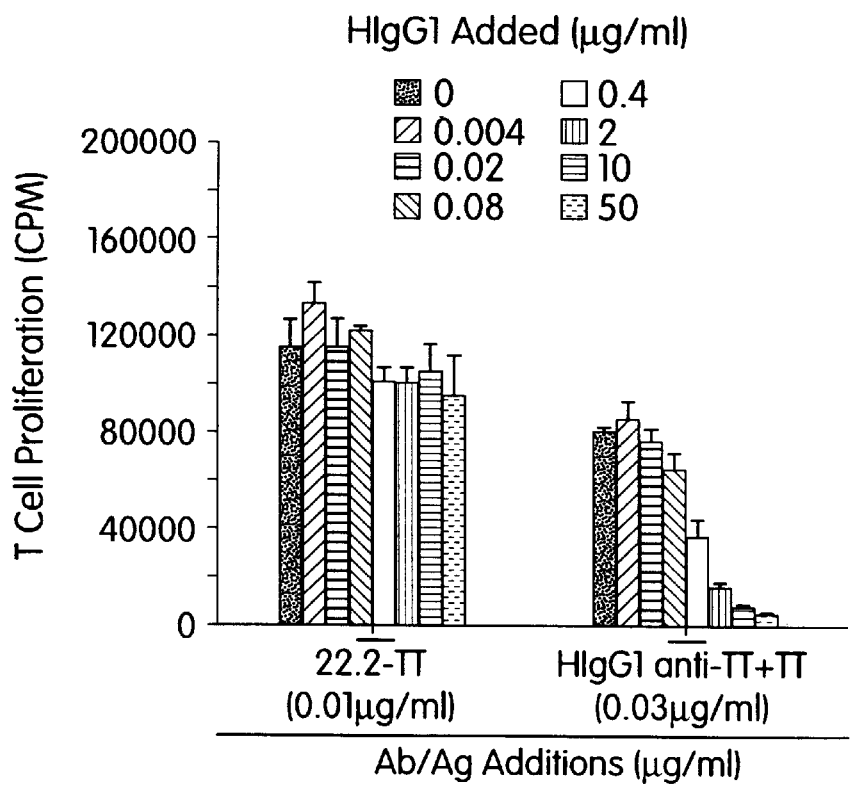

The results are shown in FIGS. 3A and 3B. In FIG. 3A, negative controls are cells and FITC goat anti-HIgG preincubated with 6 mg/ml HIgG at 4° C. (open circles), and 37° C. (open square). All samples were read on a FACSan. Data are expressed as mean fluorescence of three replicates±S.D.

Monocytes used in these antigen presentation assays had HIgG present on their surface (see FIG. 3A). These results are consistent with those of Van de Winkel et al. which show that Human FcγRI binds $HIgG_1$ with high affinity, while FcγRII and FcγRIII do not (Van de Winkel et al. (1991) *J. Leukocyte Biol.* 42:511). In addition, concentrations of IgG1 anti-TT+TT which induce a 50% maximal response (shown in FIG. 1) were completely blocked by monomeric $HIgG_1$ added at concentrations which saturate FcγRI (FIG. 3A). Under similar conditions $HIgG_1$ had no significant effect on anti-FcγRI(22.2)-TT-enhanced antigen presentation at concentrations of HIgG five-fold higher than those that block $IgG_1$ anti-TT-enhanced antigen presentation (FIG. 3B). In fact, mAb 22.2 is known to bind outside the ligand binding domain of FcγRI (Guyre et al. (1989) *J. Immunol.* 14:1650).

These results suggest an alternative explanation for reduced enhancement of antigen presentation through FcγRI when using HIgGI anti-TT+TT, which is that $IgG_1$-enhanced presentation is inhibited by serum IgG still bound to FcγRI.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of enhancing presentation of an antigen to an immune cell in a subject, comprising administering to the subject a complex comprising said antigen linked to an antibody or fragment thereof which binds to FcγRI on an antigen-presenting cell without prevention by the natural ligand for the receptor, wherein said complex is administered in a pharmacologically acceptable medium.

2. The method of claim 1, wherein the antigen is covalently crosslinked to the antibody.

3. The method of claim 1, wherein the antibody is a bispecific antibody having a binding affinity for FcγRI and for the antigen.

4. The method of claim 1, wherein the antibody is a heteroantibody.

5. The method of claim 1, wherein the antigen is selected from the group consisting of a viral, a bacterial, a parasitic, an allergen, a venom, and a tumor-associated antigen.

6. The method of claim 5, wherein the antigen is a surface antigen of a hepatitis virus.

7. The method of claim 5, wherein the antigen is an envelope glycoprotein of the human immunodeficiency virus (HIV).

8. The method of claim 5, wherein the antigen is a tumor cell antigen.

9. The method of claim 1, wherein the antigen-presenting cell is a macrophage, a monocyte or a dendritic cell.

10. The method of claim 1, wherein the complex comprises:
   (i) a first antibody, or fragment thereof which specifically binds to FcγRI without prevention by IgG; and
   (ii) a second antibody, of fragment thereof, which specifically binds the antigen.

11. The method of claim 10, wherein the complex comprises an Fab—Fab conjugate.

12. The method of claim 1, wherein the complex comprises a fusion protein comprising the antibody or fragment thereof and the antigen.

13. The method of claim 1, wherein the complex is produced recombinantly.

14. A method for targeting an antigen to an antigen-presenting cell (APC), comprising contacting the APC with a preformed complex comprising:
   and antibody or fragment thereof which binds to FcγRI on an
   antigen-presenting cell without prevention by the natural ligand for the receptor, and antigen such that the antigen is targeted to the FcγRI receptor on the APC.

15. The method of claim 14, wherein the antigen-presenting cell is a macrophage, a monocyte or a dendritic cell.

16. The method of claim 14, wherein the antibody is a bispecific antibody.

17. The method of claim 14, wherein the antigen is covalently crosslinked to the binding agent.

18. The method of claim 14, wherein the complex comprises a fusion protein comprising the antibody or fragment thereof and the antigen.

19. The method of claim 18, wherein the antigen is Her2/neu.

20. The method of claim 14, wherein the complex is produced recombinantly.

* * * * *